US011787312B2

(12) United States Patent
Main et al.

(10) Patent No.: US 11,787,312 B2
(45) Date of Patent: *Oct. 17, 2023

(54) INTELLIGENT SEAT SYSTEMS

(71) Applicant: XSENSOR Technology Corporation, Calgary (CA)

(72) Inventors: Ian Main, Calgary (CA); Melissa Elizabeth Remus Jones, Calgary (CA)

(73) Assignee: XSENSOR Technology Corporation, Calgary (CA)

( * ) Notice: Subject to any disclaimer, the term of this patent is extended or adjusted under 35 U.S.C. 154(b) by 5 days.

This patent is subject to a terminal disclaimer.

(21) Appl. No.: 17/717,038

(22) Filed: Apr. 9, 2022

(65) Prior Publication Data

US 2022/0274508 A1 Sep. 1, 2022

Related U.S. Application Data

(63) Continuation of application No. 16/741,662, filed on Jan. 13, 2020, now Pat. No. 11,370,328, which is a
(Continued)

(51) Int. Cl.
*B60N 2/02* (2006.01)
*B60N 2/00* (2006.01)
(Continued)

(52) U.S. Cl.
CPC .......... *B60N 2/0244* (2013.01); *A61B 5/0205* (2013.01); *A61B 5/18* (2013.01);
(Continued)

(58) Field of Classification Search
CPC .................................................. B60N 2/0244
See application file for complete search history.

(56) References Cited

U.S. PATENT DOCUMENTS 5,657,499 A 8/1997 Vaughn et al.
7,125,077 B2 10/2006 Frank
(Continued)

OTHER PUBLICATIONS

Kamiya, K. et al., "Sitting Posture Analysis by Pressure Sensors," 19th International Conference on Pattern Recognition, ICPR 2008, 2008, pp. 1-4, 8-11.
(Continued)

*Primary Examiner* — Michael A Berns
(74) *Attorney, Agent, or Firm* — Fenwick & West LLP

(57) ABSTRACT

An ISS is a seating system that actively adjusts to improve an occupant's comfort, performance, and safety in a specific driving environment. The ISS determines the occupant's posture, position on the seat surface, and/or physiological state, for example, by applying a machine vision process. The ISS can further determine a driving environment. The ISS adjusts its settings and settings of the vehicle according to one or more factors such as an occupant's posture, the occupant's physiological state, the occupant's preferences, and/or the driving environment. The ISS can include a state machine that determines a current state and determines if a change has occurred such that the system should shift to another state that best suits this change. The ISS makes adjustment according to system settings associated with the best suitable state.

20 Claims, 7 Drawing Sheets

Related U.S. Application Data continuation of application No. 15/469,415, filed on Mar. 24, 2017, now Pat. No. 10,562,412.

(60) Provisional application No. 62/313,054, filed on Mar. 24, 2016.

(51) Int. Cl.

| | | |
|---|---|---|
| *B60N 2/04* | (2006.01) | |
| *B60N 2/22* | (2006.01) | |
| *B60N 2/16* | (2006.01) | |
| *B60N 2/64* | (2006.01) | |
| *A61B 5/0205* | (2006.01) | |
| *A61B 5/18* | (2006.01) | |
| *A61B 5/024* | (2006.01) | |
| *A61B 5/08* | (2006.01) | |
| *A61B 5/11* | (2006.01) | |

(52) U.S. Cl.
CPC ............... *B60N 2/002* (2013.01); *B60N 2/04* (2013.01); *B60N 2/16* (2013.01); *B60N 2/22* (2013.01); *B60N 2/643* (2013.01); *A61B 5/024* (2013.01); *A61B 5/0816* (2013.01); *A61B 5/11* (2013.01); *A61B 2562/0247* (2013.01); *B60N 2002/0268* (2013.01)

(56) References Cited

U.S. PATENT DOCUMENTS

| | | |
|---|---|---|
| 7,248,996 B2 | 7/2007 | Uenishi et al. |
| 7,397,382 B2 | 7/2008 | Ikegami et al. |
| 7,740,096 B2 | 6/2010 | Bothe et al. |
| 7,918,144 B2 | 4/2011 | Saitoh et al. |
| 8,477,039 B2 | 7/2013 | Gleckler et al. |
| 8,725,311 B1 | 5/2014 | Breed |
| 8,820,782 B2 | 9/2014 | Breed et al. |
| 9,682,622 B2 | 6/2017 | Kim et al. |
| 9,751,534 B2 | 9/2017 | Fung et al. |
| 9,795,322 B1 | 10/2017 | Karunaratne et al. |
| 9,808,084 B2 | 11/2017 | Di Censo et al. |
| 9,848,814 B2 | 12/2017 | Benson et al. |
| 10,086,728 B2 | 10/2018 | White et al. |
| 10,562,412 B1* | 2/2020 | Main ................... A61B 5/0205 |
| 11,370,328 B2* | 6/2022 | Main ................... B60N 2/643 |
| 2013/0012789 A1 | 1/2013 | Horseman |
| 2014/0276090 A1 | 9/2014 | Breed |
| 2016/0001781 A1 | 1/2016 | Fung et al. |
| 2016/0089059 A1 | 3/2016 | Hu |
| 2016/0113583 A1 | 4/2016 | Min |
| 2020/0148076 A1 | 5/2020 | Main et al. |
| 2022/0274508 A1* | 9/2022 | Main ................... A61B 5/6893 |

OTHER PUBLICATIONS

Koshimizu, S. et al., "Authentication Based on Seating Pressure Distribution Using the MT System," J. Teknologi, 2014, pp. 87-90, vol. 68, No. 4.

Meyer, J. et al., "Design and Modeling of a Textile Pressure Sensor for Sitting Posture Classification," IEEE Sensors Journal, Aug. 2010, pp. 1391-1398, vol. 10, No. 8.

Zhu, M. et al., "Template-Based Recognition of Static Sitting Postures," Proceedings of the 2003 Conference on Computer Vision and Pattern Recognition Workshop, CVPRW03, IEEE, 2003, pp. 29-34.

* cited by examiner

INTELLIGENT SEAT SYSTEMS

CROSS-REFERENCE TO THE RELATED APPLICATIONS

This application is a continuation of U.S. patent application Ser. No. 16/741,662, filed Jan. 13, 2020, which is a continuation of U.S. patent application Ser. No. 15/469,415, filed on Mar. 24, 2017 (now U.S. Pat. No. 10,562,412 issued on Feb. 18, 2020), which claims the benefit of U.S. Provisional Patent Application Ser. No. 62/313,054, filed Mar. 24, 2016. All these applications are incorporated herein by reference in its entirety for all purposes.

BACKGROUND OF THE INVENTION

1. Field of the Invention

This invention relates generally to seating systems.

2. Description of the Related Art

It is well known that sitting for prolonged periods of time is a major cause of back pain. Choosing the right seating system and adjusting the seating system to proper positions are important to good rests and a healthy body. However, it is difficult to adjust seating systems to provide the right support and comfort for users in different circumstances because people have different needs when sitting down performing different activities. Besides being uncomfortable, poor seating ergonomics over time may disrupt persons' alertness, restfulness, and productivity; and even damage spinal structures. There is always a need for better seating systems.

SUMMARY

One example of an improved seat system is referred to herein as an Intelligent Seat System (ISS). The ISS is a seating system that actively adjusts to improve an occupant's comfort, performance, and/or safety in a specific driving environment. The ISS measures pressure surface values of an occupant on a seat surface and determines the occupant's posture, position on the seat surface, and/or physiological state. In one embodiment, the ISS applies a machine vision process to detect and identify an occupant, detect the occupant's posture and position, track regions of high pressure, and/or determine the occupant's physiological state. The ISS can further determine a driving environment, for example, based on measurements generated or data received. For example, the ISS measures a temperature and/or a humidity surrounding the seat support system, measures forces and vibrations exerted on the seat support system, and/or receives navigation data, radar data, weather report, vehicle safety data, and the like, from the vehicle or other sources. The ISS can be communicatively coupled to the vehicle and can also be integrated with the vehicle. The ISS provides an initiation process that allows an occupant to provide the occupant's preferences.

The ISS adjusts its settings and settings of the vehicle according to one or more factors such as an occupant's posture, the occupant's physiological state, the occupant's preferences, and/or the driving environment. The ISS can include a state machine that determines a current state and determines if a change has occurred such that the system should shift to another state that best suits this change. The ISS makes adjustment according to system settings associated with the best suitable state.

An ISS preferably is customizable to an individual user's needs at each moment while driving or as a passenger, and over time can be tailored to the user's preferences, habits, and body type. Actively adjusting the seating environment to the user's requirements reduces muscle and back strain, and improves comfort and posture. In another aspect, in emergency circumstances, an ISS can respond in the most appropriate manner and sequence to limit injury or discomfort according to an occupant's body position and activity. An ISS is also applicable in airlines, buses, trains, ergonomic furniture, wheelchairs or other applications.

Other aspects of the invention include methods, devices, systems, components, improvements and other technology related to the concepts described in this document.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

I. Overview of Operation

When riding in a vehicle, an occupant's posture can be divided into states such as ideal, relaxed, slouched, sleeping, and a variety of possible positions. An occupant's physiological state can be divided into states such as awake, drowsy, asleep, and a variety of possible states. To determine what posture position and/or what physiological state the occupant is in, an ISS may monitor the occupants' body position and biometric data, and combine this information with past trends. Moreover, the system can detect a driving environment surrounding and inside the vehicle. The ISS (also referred herein as the system) matches the occupants' posture, the occupant's physiological state, and/or the driving environment to appropriate system settings that include settings of a seat support system (e.g., a bolstering level, a seatback angle, a distance from a steering wheel, a seat height, a shape of a seat surface, a seat temperature, etc.) and settings of the vehicle (e.g., a temperature, a humidity, a light level of a dashboard, etc.) As described herein a "seat surface" refers to a surface of a seat support system that can include a seatback. A seat support system is also referred herein as a seat.

Figure 1:
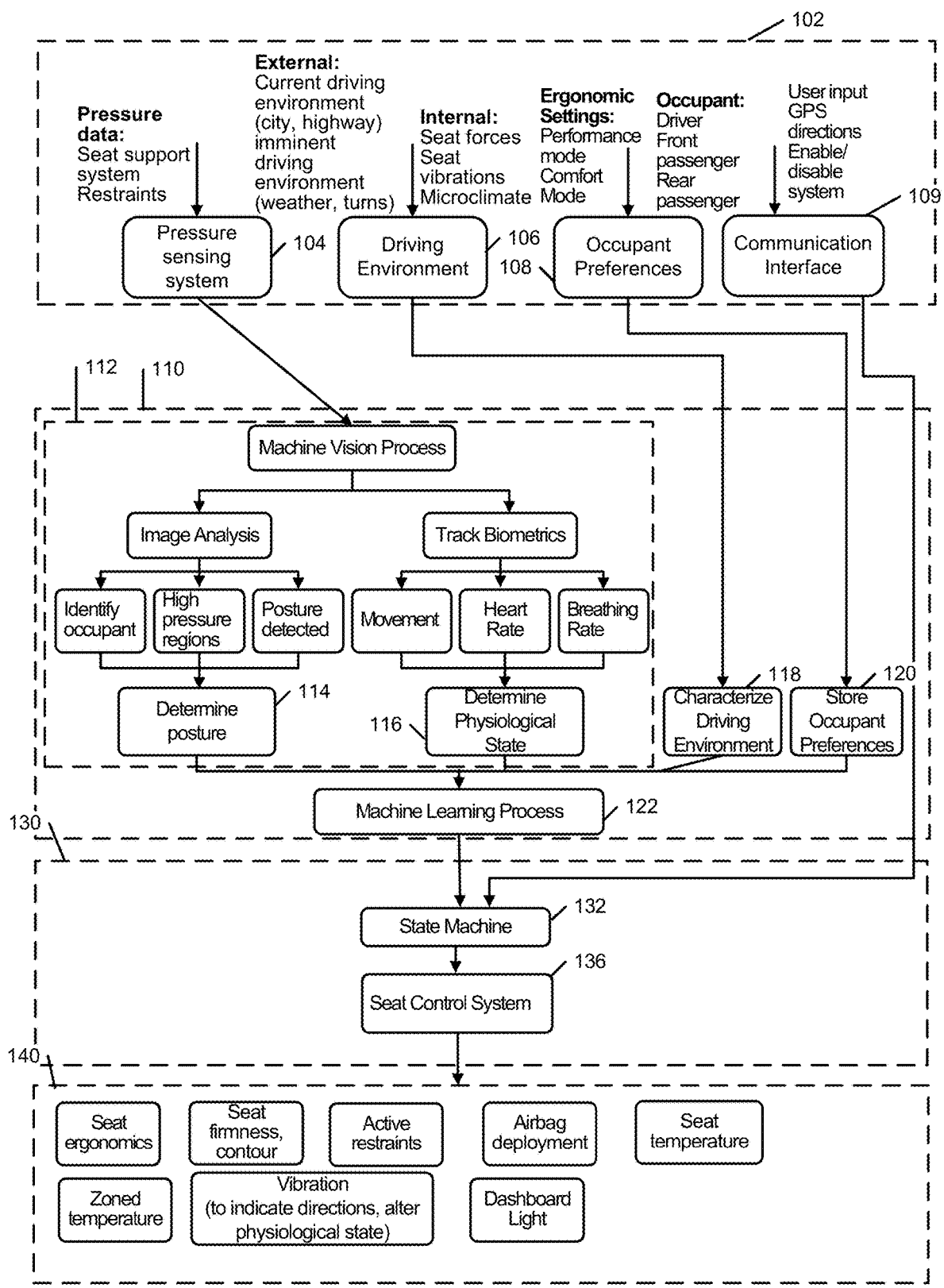
FIG. 1 is a diagram of an operation process of an example ISS.

In one example, the functions of the ISS can be categorized into cooperating subsystems and/or processes controlled by a state machine. Together, these monitor the conditions of the driving environment and the occupant, process information to determine changes, and execute control over the subsystems to improve the occupant's driving experience. FIG. 1 is a diagram of an example ISS's operation process.

A. Processes and State Control

As illustrated, an ISS employs the following three process:

1. Machine Vision Process 112
2. Machine Learning Process 122
3. State Machine Process 132

These processes operate on the input of each subsystem of the ISS to identify one or more occupants, determine their posture and physiological state, and characterize the current driving environment. The subsystems of the ISS are further described below.

1. Machine Vision Process

In the illustrated example, the following subsystems employs a machine vision process 112:

a. Occupant Identification System 114: The occupant identification system 114 detects one or more occupants and identifies them by their physical attributes. For an occupant, the occupant identification system 114 detects the occupant's posture and regions of high pressure. The physical attributes include anatomical features such as ischial tuberosities, greater trochanters, lumbar regions, leg positions, and the like. The occupant identification system 114 can differentiate a human from an inanimate object and can also identify an occupant's body type (e.g., small, medium, or large). As further described below, the occupant identification system 114 can apply a machine vision process to pressure images to detect and identity an occupant and also detect an occupant's posture. The machine vision process analyzes images to determining a "seating signature" (e.g., image features) thereby to identify an occupant and also to detect his or her posture and regions of high pressure. For an occupant that is known, an ISS considers information about the occupant such as the occupant's preferences, past history such as medical conditions (e.g., susceptible to back pain, or should not drive at night) when determining a suitable system setting.

b. Physiological State Detection System 116: The physiological state detection system 116 determines an occupant's physiological state. An occupant's physiological state such as alertness can be quantified by measuring the occupant's heart rate (HR), breathing rate (BR), and body movement. The measured values are processed to classify (e.g., quantify) a physiological state of the occupant as to a level of alertness or wakefulness and/or drowsiness. For occupants that are passengers, drowsy or sleeping states may be desired for long drives.

2. Machine Learning Process

A machine learning process 122 refines determining and adjusting settings of an ISS for occupants. For an occupant, the machine learning process 122 analyzes a history of the occupant's posture, physiological states, the driving environment, and/or the occupant's preferences. The machine learning process 122 compares and correlates current settings of a seat support system, current settings of an vehicle, and environmental conditions to past trends to refine settings associated with each state thereby to improve driving experiences.

3. State Machine Process and Control

A state machine 132 determines a current state of an ISS according to an occupant's posture, a time, a driving environment, and the occupant's activities. The occupant's posture, the occupant's activity state, the driving environment, and/or the occupant's preferences can be used to determine the current state of the Intelligent Seat System. The previous state and a trigger, such as change in the occupant's posture, activity state, and/or preferences, and/or the driving environment can be used to determine a state that best suits this change. The state machine 132 can further determine system settings associated with the best suitable state. The ISS transitions to the best suitable state, for example, by adjusting the seat support system and/or the vehicle (e.g., a temperature, a light level of the dashboard, etc.) according to the determined system settings.

B. Subsystems

As illustrated in FIG. 1, the functions of this example ISS can be divided into an input stage 102, a processing stage 110, a control stage 130, and an output stage 140. As further described below, the subsystems include sensors that actively monitor a current state of the ISS and controlled actuators to adapt the ISS to a state suitable for an occupant and/or the driving environment.

In one embodiment, an ISS includes a seat support system, an occupant monitoring system, a driving environment monitoring system, and a seat control system. The seat support system is adjustable and includes a seat surface supporting an occupant. The occupant monitoring system detects an occupant and the occupant's posture. The occupant monitoring system can further identify the occupant or detect the occupant's physiological state. The driving environment monitoring system detects a driving environment. The seat control system is coupled to the seat support system, the occupant monitoring system, and the driving environment monitoring system. The seat control system adjusts the seat support system according to the occupant's posture, the driving environment, and/or the occupant's physiological state.

Pressure sensing system 104: An occupant's pressure data is collected from a system of pressure sensors. The pressure sensors measure surface pressure values of an occupant on a seat surface and/or on a seatbelt. The pressure sensors can be integrated with (e.g., embedded in) a seat support system to measure surface pressure values of an occupant on a seat surface supporting the occupant. A seatbelt can include integrated pressure sensors to measure surface pressure values of an occupant on the seatbelt, which provides a basis for determining a tightness level of the seatbelt. The measured pressure values can be processed (e.g., by using a machine vision process 112) to:

1. Detect an occupant,
2. Identify the occupant if the occupant is known,
3. Detect the occupant's posture and position in the seat support system, 4. Track high pressure areas (e.g., corresponding to bony prominences), and/or
5. Detect the occupant's body movement, activities, and/or physiological state (alert, drowsy, asleep).

Driving environment monitoring system 106: The driving environment monitoring system 106 monitors a driving environment including conditions inside and outside a vehicle.

The driving environment monitoring system 106 receives data from sensors and information systems (e.g., GPS, radar, antennas, etc.) integrated with the vehicle and determines an external environment. Example received data includes navigation data, radar data, vehicle safety data, weather data, road condition data, or external light level data. The received data can be processed to determine:
1. Current driving environment:
   a. Highway,
   b. City,
   c. Racing,
   d. Off-road, and/or
   e. Out of Control; and
2. Imminent driving environment:
   a. Sharp turns,
   b. Increases or decreases in speed limit, and/or
   c. Weather conditions affecting driving environment; and/or
   d. Obstacles along a driving path.

In some embodiments, the driving environment monitoring system 104 includes an accelerometer, a temperature sensor, and/or a humidity sensor that can be integrated with the seat support system. The accelerometer measures forces and vibrations exerted on the seat support system. The temperature sensor measures a temperature of the seat support system and/or an ambient temperature inside the vehicle (e.g., in an area surrounding the seat support system.) The humidity sensor measures an ambient humidity level inside the vehicle (e.g., in an area surrounding the seat support system.) The measured values can be analyzed to determine:
1. A lateral acceleration and/or G forces experienced by the occupant,
2. The temperature and/or humidity surrounding the seat support system, and/or
3. Vibration levels experienced by the seat support system.

Moreover, the driving environment monitoring system 106 can estimate an occupant's core skin temperature, for example, by analyzing temperature measurements by a temperature sensor integrated with the seat support system. As further described below, the measured occupant's core skin temperature is one of the factors used for adjusting temperature thereby to achieve transitions to a suitable state.

Occupant preferences system 108: An initial calibration process allows occupants to configure preferred settings such as a setting of a seat support system. The preferred settings can be stored in a memory. These preferred settings include configurations for:
1. an occupant as a driver,
2. the occupant as a passenger,
3. a performance mode, and/or
4. a comfort mode.

Communication Interface 109: The communication interface 109 enables an occupant to interact with an ISS. For example, an occupant can configure an ISS or access its settings via the communication interface 109. The communication interface 109 further enable an occupant to interact with a vehicle. For example, an occupant can set up a navigation destination. The communication interface 109 can be integrated with a vehicle.

Seat control system 136: The seat control system 136 can adjust various aspects of a seat support system such as seat ergonomics, seat firmness and contour, and/or seat temperature according to settings associated with a suitable state. For example, the seat control system 136 adjusts a surface, a distance from a steering wheel, a seat height (i.e., a height of the surface of the seat support system), a seatback angle, and/or a temperature of a seat support system. The seat control system 136 can adjust different regions of the seat support system separately.

The seat control system 136 can adjust a vibration of a seat support system. In one embodiment, the seat support system includes a vibration element integrated with a surface of the seat support system. The vibration element vibrates and causes the seat surface to vibrate thereby to alert and/or signal an occupant. The vibration element can also generate different vibration patterns representing different instructions, for example, using haptic technologies.

The seat control system 136 can adjust settings of a vehicle. For example, the seat control system 136 adjusts safety restraints such as a seatbelt or an airbag of a vehicle. As such, the seat control system 136 can improve safety levels. As another example, the seat control system 136 adjusts a temperature setting of a vehicle such as a target temperature for a particular zone, a mode (e.g., head, head and feet, etc.), a fan speed, or a fan direction, etc. As a further example, the seat control system 136 adjusts a light level (e.g., a color or a brightness) of a dashboard of a vehicle. By adjusting a temperature and/or lighting inside a vehicle, the seat control system 136 can regulate an occupant's physiological state to a desired state. The communication control system 134 is communicatively coupled to a vehicle (e.g., an in-car console).

II. Driving States and the State Machine

An ISS functions by transitioning amongst various states and sub-states. A state or a sub-state corresponds to a driving environment, an occupant's posture, the occupant's physiological state, and/or the occupant's preferences. A trigger such as a body movement or detection of an obstacle signals the system to transition from a current state to a new state best suited for the change. An ISS features a manual mode, where the settings and transitions between each state can be initiated by the occupant, or an automatic mode, which learns and adapts to the occupant over time.

An ISS differentiates a driver and a passenger according to locations of seats in a vehicle. A driver occupant must always be alert, whereas a passenger occupant may prefer to rest or sleep. Therefore, an ISS can determine that different states are suitable for a driver and for a passenger. An occupant can configure different modes such as a comfort mode, a performance mode, and/or a safety mode. Comfort modes encompass traditional transportation environments including city driving and highway driving. Performance modes apply to high speed driving (e.g., racing) or rough terrain driving (e.g., off-road) environments. Safety modes apply to loss of control situations or adverse conditions (e.g., extreme weather).

Figure 2:
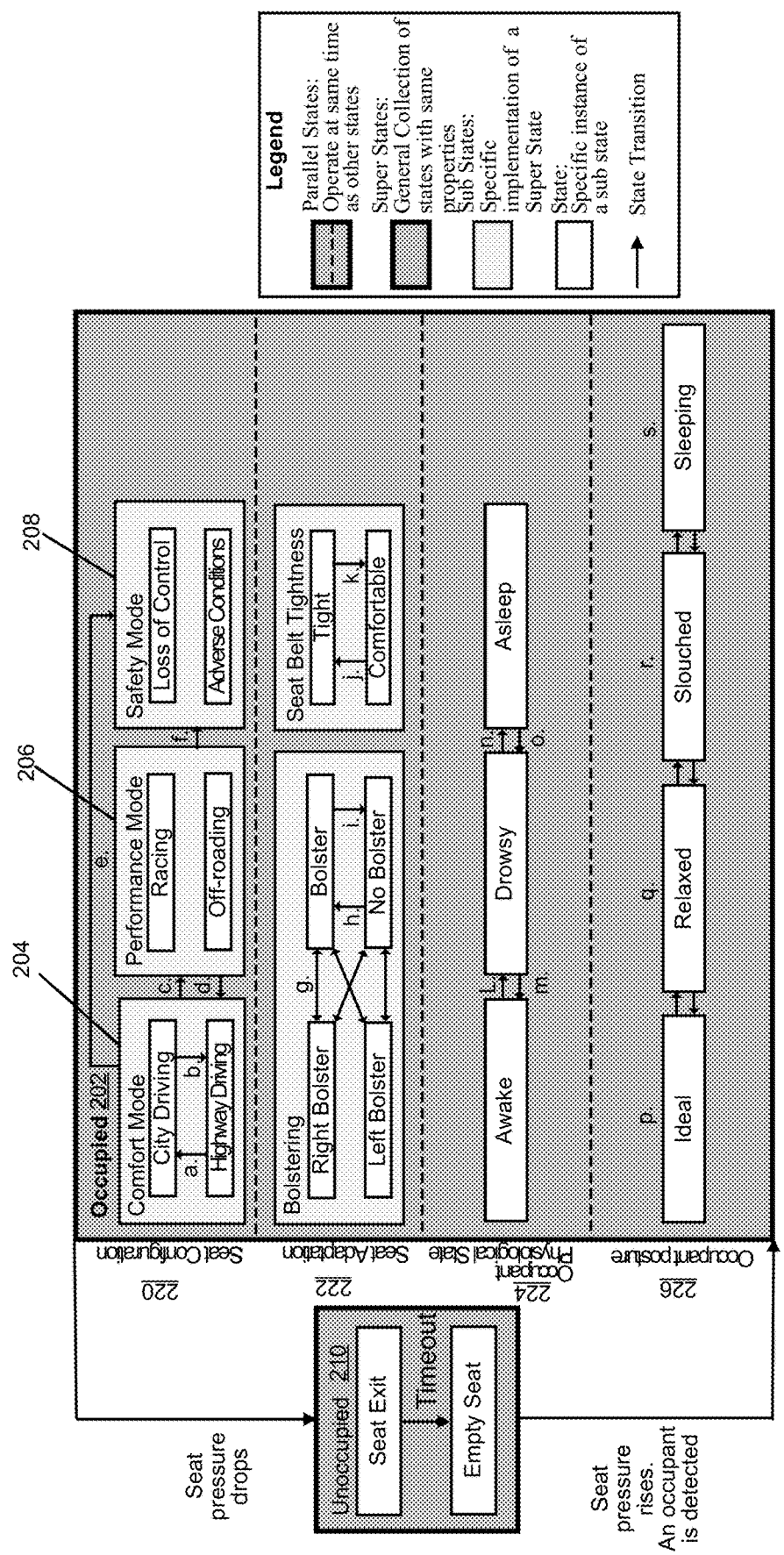
FIG. 2 is an example state machine diagram for an ISS.

To simplify the operation, the ISS may be organized into hierarchal states: broad conditions containing more specialized instances. FIG. 2 illustrates an example organization of these states and a summary of their features.

When a person is seated, an ISS transitions to an occupied state 202. The occupied state 202 includes and is defined by a number of concurrent Super States:

1. Seat Configuration State 220,
2. Seat Adaptation State 222,
3. Occupant Physiological State 224, and
4. Occupant Posture State 226.

The seat configuration state 220 corresponds to an overall ergonomic position of an ISS for a current driving environment. The seat adaptation state 222 corresponds to adjustments needed for an imminent or unexpected driving condition. The occupant physiological state 224 corresponds to an alertness level of an occupant. The occupant posture state 226 corresponds to a posture of the occupant which corresponds a comfort and support level of the ISS.

Within each super state, the system responds to changes in the driving environment, the occupant's physiological state, the occupant's posture, and/or the occupant's preferences to determine a current state and a desired state. The system adjusts based on the desired state. In some embodiments, if an emergency situation such as adverse weathers or a loss of vehicle control arises, the ISS transitions to a safety state to alert and protect the occupant.

As illustrated, within the Seat Configuration State 220, an ISS can transition between a comfort mode and a performance mode, can transition from the comfort mode to a safety mode, or transition from the performance mode to the safety mode. An ISS can transition from the comfort mode to the performance mode according to a user instruction or when the driving environment involves high speed racing or rough terrain, which can be determined from navigation data and/or radar data. The ISS increases a bolstering level of a seat support system. Likewise, the ISS can transition from the performance mode to the comfort mode according to a user instruction or when the driving environment involves city or highway driving, which can be determined from navigation data. The information includes navigation data received from a GPS. The ISS decreases a bolstering level of a seat support system. Adjusting a bolstering level of the seat support system can adjust an amount of lateral support provided to the occupant.

An ISS can transition from the comfort mode (or performance mode) to the safety mode automatically when there is a loss of control or adverse conditions. The information can be determined from navigation data gathered by the vehicle's GPS, radar data collected by the vehicle's forward-facing radar, and/or environment condition data.

Within the comfort mode, an ISS can transition from a city driving state to a highway driving state when the vehicle is slowing down and leaving a highway. The ISS adjusts the seat closer to the steering wheel and more upright. The ISS can adjust or maintain a bolstering level of the seat to a reduced level or to a level configured by an occupant. Vice versa, an ISS can transition from the highway driving condition to a city driving condition when the vehicle is speeding up and is entering a highway. The ISS adjusts the seat further away from the steering wheel and more declined. The ISS can adjust or maintain a bolstering level of the seat to a reduced level or to a level configured by an occupant. The information includes navigation data received from a GPS.

Within the Seat Adaptation State 222, an ISS can increase an overall bolstering level of the seat support system when the terrain becomes rough imminently or unexpectedly. The ISS can increase a right bolstering level or a left bolstering level of the seat support system when there are corners along the driving path imminently or there is unanticipated large forces. The ISS can decrease a bolstering level of the seat support system to normal when no seat adaptation is required, for example, in an imminent driving environment.

Additionally, within the Seat Adaptation Super State 222, an ISS can adjust a seat belt's tightness level. For example, an ISS can tighten a seat belt when obstacles are detected along the driving path or that the vehicle is deaccelerating to exit a highway. The ISS can adjust the tightness level of the seat belt to a comfortable level when no seat adaptation is required. The information includes navigation data received from a GPS, radar data received from a radar, and/or accelerometer data.

Within the Occupant Physiological State 224, an ISS transitions between an awake state and a drowsy state, and between the drowsy state and asleep state. When an occupant enters a seat, the ISS determines that the occupant is awake and transitions to the awake state. When the occupant's HR level, BR level, and body movement level decrease, the ISS determines that an occupant is drowsy and transitions to the drowsy state. When the occupant's HR level, BR level, and body movement level continue to decrease, the ISS determines that an occupant is asleep and transitions to the asleep state. Vice versa, from the asleep state, the ISS transitions to the drowsy state when the occupant's HR level, BR level, and body movement level increase indicating that the occupant has awaken. When the occupant's HR level, BR level, and body movement level continue to increase, the ISS determines that an occupant is awake and transitions to the awake state.

Within the Occupant Posture State 226, an ISS can transition between an ideal state and a relaxed state, between the relaxed state and a slouched state, and between the slouched state and a sleeping state. If an occupant's posture is determined to be ideal, the ISS shifts to the ideal state. The occupant's posture is ideal when pressure distribution across the seat surface is substantially uniform and symmetrical. If the occupant's posture is determined as relaxed when the contact area on the seat surface increases and the pressure distribution across the seat surface remains substantially uniform and symmetrical, the ISS transitions to the relaxed state. If the occupant's posture is determined as slouched when the contact area on the seat surface continues to increase and the pressure distribution across the seat surface is uneven and asymmetrical, the ISS transitions to the slouched state. If the occupant's posture cannot be identified because the pressure data is not correlated to any predetermined posture position, the ISS determines that the occupant is sleeping and transitions to the sleeping state.

When a person leaves the seat support system, the system transitions to an unoccupied state 210. In some embodiments, when an occupant leaves a seat, the ISS reduces a bolstering level to a normal level.

III. Machine Vision

Machine vision algorithms are used to analyze the image acquired from the pressure sensing system embedded in the seat surface. This process derives important metrics about an occupant such as the occupant's identity, posture, comfort, or physiological state. The metrics can be used to determine a state of an ISS.

A. Image Analysis

1. Occupant Detection and Identification

Figure 3:
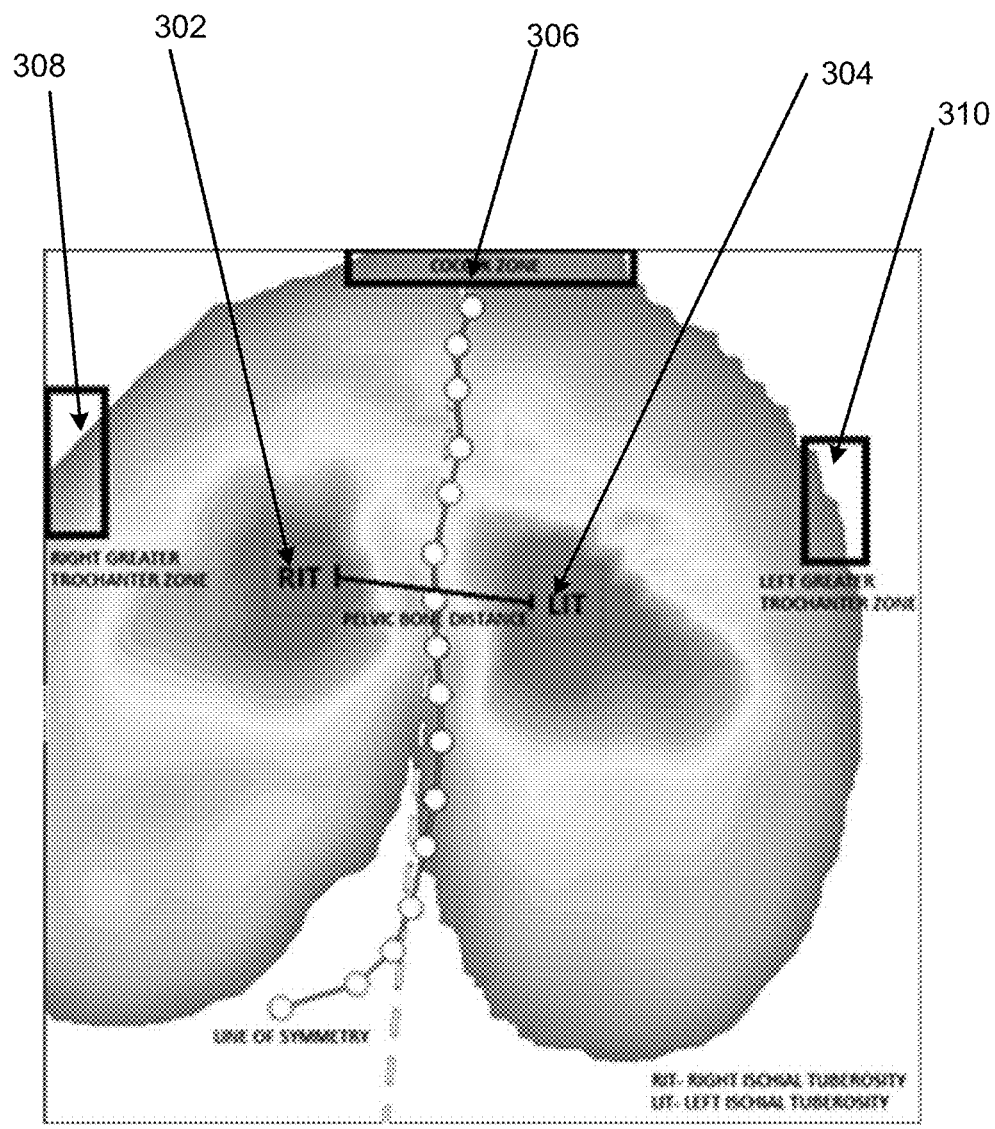
FIG. 3 shows a representative pressure image for a sitting posture.

An occupant can be detected and identified by analyzing a pressure image of the occupant. The pressure image can be generated based on pressure data such as surface pressure values of the occupant on the seat surface. FIG. 3 illustrates an example pressure image for a sitting posture. The machine vision process extracts features such as image features. Image features may include a maximum pressure, contact area, average pressure, shape features, pelvic bone distance, symmetry, and other distinguishing metrics. A mahalanobis distance, and/or an identification of a specific zone (e.g., a right or left ischial tuberosities zone 302, 304, or a right or left greater trochanter zone 308, 310, and coccyx zone 306). A feature space is constructed using the features collected from the occupant. The feature space can be compared to reference feature spaces to determine a degree of similarity. An occupant is identified when there is a match. The reference feature spaces are constructed for occupants whose identities are known. For example, reference feature spaces can be constructed by analyzing pressure values collected for users in their normal driving posture.

2. Posture Detection

An occupant's posture can be detected by analyzing a pressure image of the occupant on the seat surface. In some embodiments, an ISS selects a predetermined posture as the occupant's posture. For example, the ISS classifies a pressure image into a posture category by comparing the pressure image to reference pressure images corresponding to different posture categories. The pressure image is classified into a particular posture category when the pressure image is determined to be most similar to the reference pressure image corresponding to that particular posture category. A pressure image can be classified into multiple posture categories. An intermediate position of the multiple posture categories is the occupant's posture. To classify a pressure image, a machine vision process extracts geometric features from the pressure image and compares the extracted geometric features to those of reference pressure images. In one embodiment, the posture categories include:

1. Upright,
2. Right-leaning,
3. Left-leaning,
4. Forward-leaning,
5. Back-leaning,
6. Right leg crossed,
7. Left leg crossed,
8. Sitting on forward edge, and
9. Slouching, The machine vision process can further extract regions of high pressure from a pressure image. A region of high pressure corresponds to an area in the pressure image of which the surface pressure values above a threshold value. The machine vision process can track a region of high pressure over time. An ISS considers an occupant's posture and/or a region of high pressure when determining a suitable state. The ISS can adjust a seat surface such as its contour according to an occupant's posture and/or a region of high pressure. For example, the surface can be adjusted to improve the occupant's posture or to prevent forming a region of high pressure for a threshold time interval.

B. Biometric Tracking

An ISS can determine an occupant's physiological state, for example, by analyzing the occupant's biometrics and body movement. In some embodiments, an ISS uses a Ballistocardiography (BCG) method that extracts heart rate (HR) and breathing rate (BR) by measuring oscillatory motions in a pressure image. These motions are caused by the action of the heart, and the motion of a person's thorax while breathing. The overall pressure intensity oscillates with this periodic motion, the pressure over time signal can be processed and filtered to obtain measurements as accurate as 0.4% for heart rate and 1.5% for breathing rate. Erratic changes can also be quantified as the occupant's movements.

The machine vision process analyzes a pressure image to determine a location of the occupant's thorax thereby to determine a thorax area. The pressure image includes measured surface pressure values. The process analyzes time variations in the measured surface pressure values in the thorax area to determine periodic oscillations of the occupant's thorax. The process determines a value of at least one of a heart rate, a breathing rate, and a body movement of the occupant from the determined periodic oscillations. The process can determine the occupant's physiological state based on the determined value.

Figure 4:
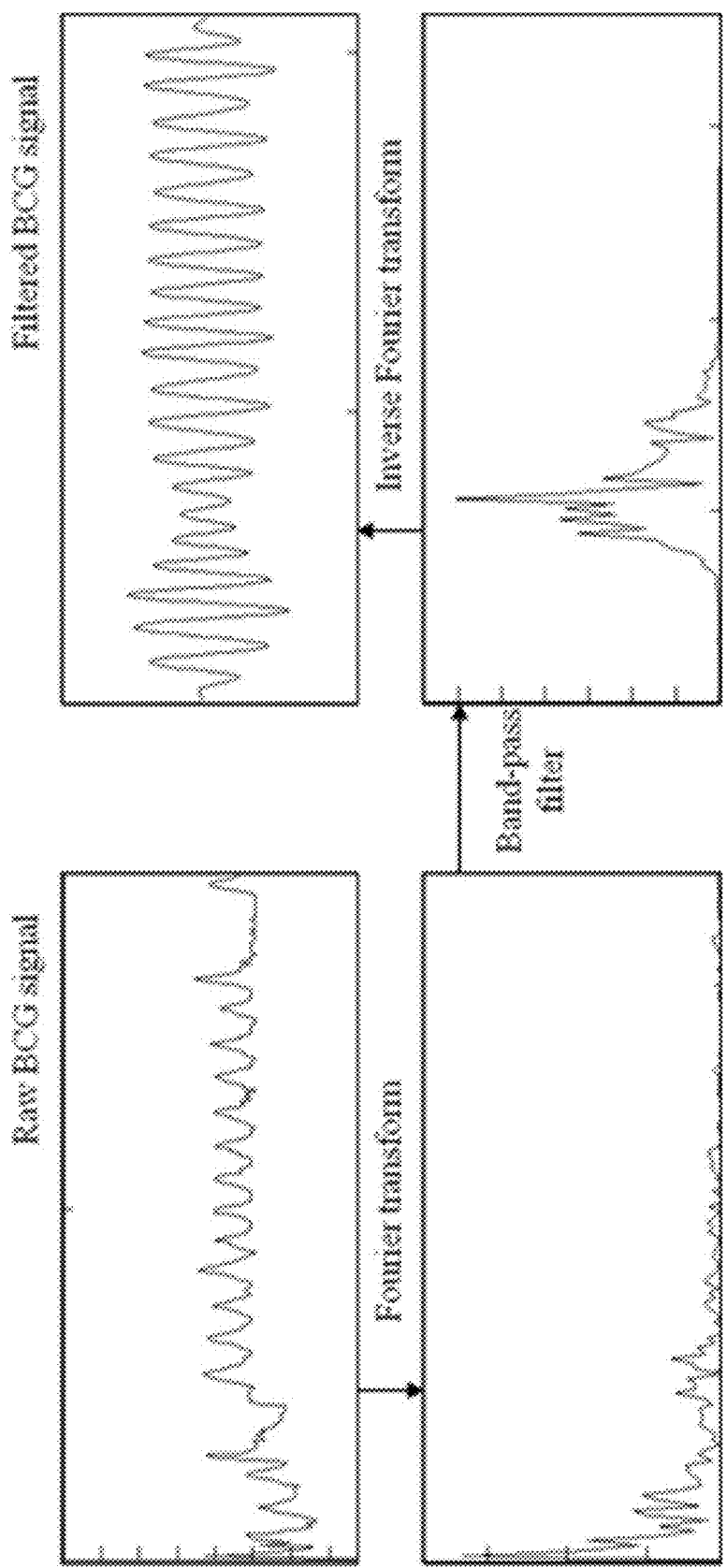
FIG. 4 illustrates a process for extracting heart rate (HR) and breathing rate (BR) from pressure data.
Figure 5:
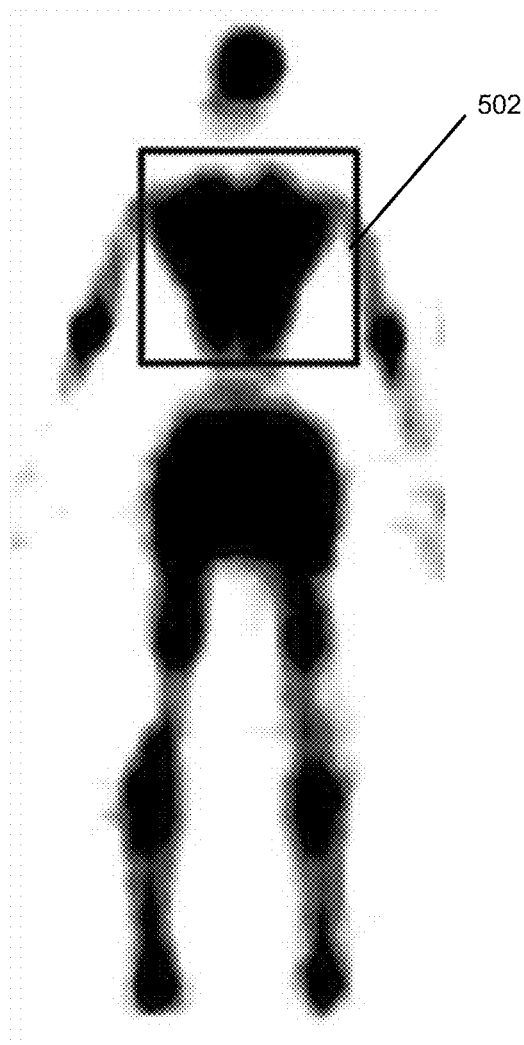
FIG. 5 is a machine vision image illustrating segmenting the thorax region.

One process for determining breathing and heart rate is as follows (see FIG. 4):

1. Scan entire surface at 1 Hz;
2. Use machine vision to identify the thorax region 502 (see FIG. 5);
3. Oversample this area at 10+ Hz;
4. Track the motion of the thorax center of pressure (COP) along the length of body;
5. Find calm periods in the signal by segmenting out movement artefacts, i.e. periods where the COP movement has higher than average energy;
6. Run the calm signals through a band-pass filter:
   a. Heart Rate: 0.5-1.5 Hz (30-90 beats per minute) and
   b. Breathing Rate: ⅙-⅓ Hz (10-20 cycles per minute);
7. Find peaks in the signals and calculate time between each one (inter-beat interval, "IBI"); and
8. Calculate breaths or beats per minute.

Decreases in heart rate, breathing rate and movement typically indicate relaxation of an occupant's physiological state, for example, from being alert, to relaxed, and eventually asleep. An ISS considers an occupant's physiological state when determining a suitable state. The ISS can adjust its settings (e.g., a temperature of a seat support system, or an ambient temperature of a vehicle) according to the occupant's physiological state.

IV. Intelligent Seat System Structure and Features

A. Ergonomic Adjustments

Figure 6:
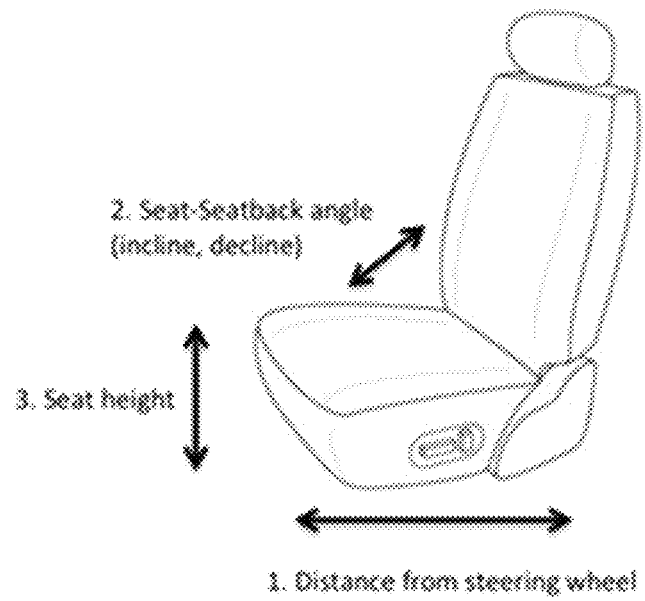
FIG. 6 illustrates example ergonomic adjustments of an example ISS.
Figure 7:
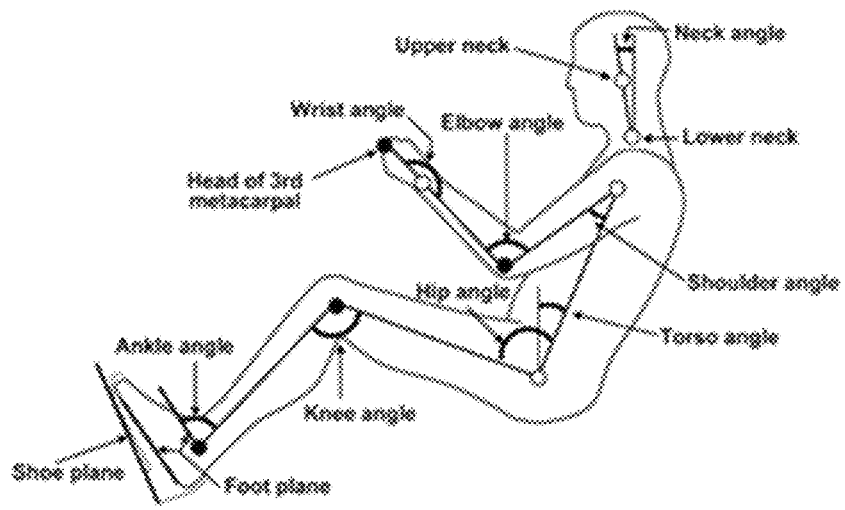
FIG. 7 illustrates example reference joint angles used to adjust an example ISS.

An ISS facilitates an occupant in adjusting a seat support system thereby to achieve an occupant's joint angles in preferred ranges. FIG. 6 illustrates example ergonomic adjustments of an example ISS. As illustrated, ergonomic adjustments of a seat support system include adjusting a distance of a seat surface from the steering wheel, a seatback angle, and/or a seat height. A seat support system can be adjusted such that joints of an occupant supported achieve preferred joint angles. For example, in one embodiment, a reference shoulder angle has a value selected from 7-69 degrees, a reference elbow angle is a value selected from 86-164 degrees, a reference wrist angle is a value selected from 130-216 degrees, a reference hip angle is a value selected from 68-127 degrees, a knee angle is a value selected from 95-157 degrees, and an ankle angle is a value selected from 77-115 degrees. Example ergonomic adjustments of an ISS to achieve optimal joint angles are shown in FIG. 7.

B. Adjustable Seat Support Surface

Figure 8:
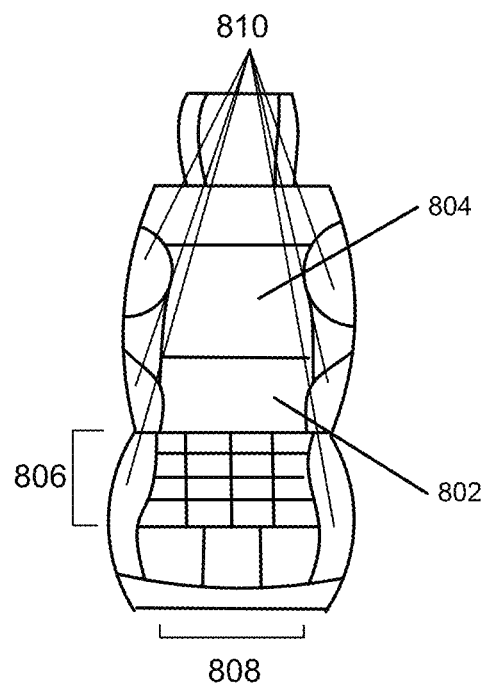
FIG. 8 illustrates air bladders located in an example ISS.

An ISS can adjust a seat support system such as a seat surface (e.g., a firmness, a shape, a contour, a seatback profile etc.) or a bolstering level to improve comfort and spine support, and/or to reduce lateral movement of an occupant. A seat support system includes adjustable air bladders integrated with the seat support system. Air bladders can be adjusted to adjust the seat surface's surface and/or a bolstering level. Air bladders serve two purposes (see FIG. 8): 1) pressure relief and posture support, and 2) lateral support.

1. Pressure Relief and Posture Support

A connected air bladder-array in a base of a seat support system can be adjusted to achieve a substantial uniform distribution of pressure across the cells of the array that are in an occupant's preferred range. Even pressure distribution across the occupant's buttocks results in an overall reduction of peak pressures, and increased comfort. High pressure points disrupt blood flow to surrounding soft tissues, which may cause discomfort.

Additionally, air bladders in specific areas (e.g., lumbar, or thoracic) can be adjusted to provide posture support in those regions. As such, the occupant's posture is improved and fatigue in the muscle groups supporting the spine can be decreased. Air bladders in those regions can be independently adjustable according to a state suitable for an occupant's posture, physiological condition, and/or preferences, and/or a driving environment.

For example, air bladders in region 802 are adjusted to provide lumbar support. Air bladders in region 804 are adjusted to provide cervical spine support. Air bladder arrays in region 806 are adjusted to equalize firmness across air cells to achieve even pressure distribution. Air bladders in region 808 are adjusted to relive pressure points in thighs.

2. Lateral Support

A level of bolstering 810 can be adjusted to reduce lateral movement of an occupant while driving. An ISS can automatically increase a level of bolstering during performance conditions such as in racing and off-roading. An ISS can automatically decrease a level of bolstering during comfort conditions such as city and highway driving. A level of bolstering can also be adjusted to provide seat adaptation to reduce discomfort that may arise in imminent driving conditions such as sharp turns, quick acceleration and hard breaking. The level of bolstering can be adjusted according to an occupant's preferences. An ISS minimizes a level of bolstering when an occupant entering and exiting a vehicle.

C. Seat Structure and Internal Environment Monitoring

Figure 9:
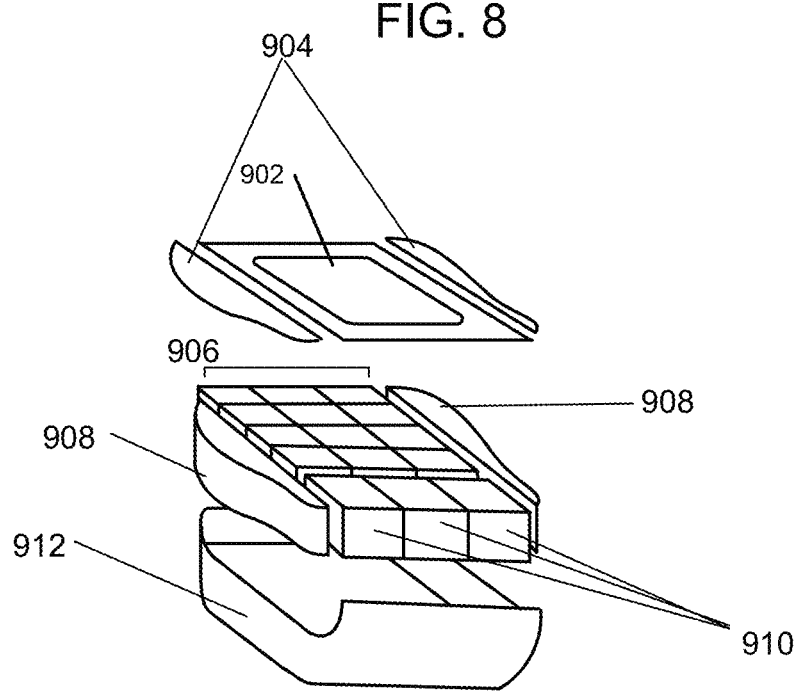
FIG. 9 is an exploded view showing layers of an example ISS.

FIG. 9 illustrates an example mechanical structure of a seat support system included in an ISS. The seat support system includes a flexible pressure sensing mat 902 that generates pressure data. The flexible pressure sensing mat 902 measures surface pressure, generates surface pressure measures, and provides the measurements to another ISS's component such as an occupant monitoring system and/or a state machine. The surface pressure values may also be presented to the occupant, for example, through a communication interface. The seat support system includes vibration elements 904. The vibration elements 904 vibrate to alert or to signal an occupant with direction instructions or blind spot detections. The seat support system includes a layer of air bladders displaced underneath the pressure sensing mat 902 and vibration elements 904. The layer of air bladders include air bladder arrays 906 that can be adjusted to achieve equal pressure distribution under pelvis, air bladders 908 that can be adjusted to adjust a level of bolstering, and air bladder arrays 910 that can be adjusted to relieve pressure points in thigh regions. The seat support system further includes a seat base 912 that provides mechanical support for the seat support system. Other components such as a comfort layer are not shown. The comfort layer includes a thin layer of foam that covers the pressure sensor and vibration elements. The comfort layer can additionally include heating and/or cooling elements.

Pressure sensing mats are also embedded in the seatback to record posture and physiological data. An accelerometer system can be centrally located in the seat to track forces and vibrations exerted on the ISS, and a temperature module monitors the internal environment surrounding the ISS. Heating units are also embedded in the seat surface to modulate core temperature.

D. External Environment Monitoring

An ISS is connected to a number of safety and communication systems of the vehicle. An ISS can include a communication interface for interfacing with an occupant. An ISS can receive at least one of navigation data, radar data, vehicle safety data, weather data, road condition data, and external light level data from a vehicle or other sources. The received data can be used to determine an external environment. For example, the vehicle's GPS can provide GPS data to an ISS. The GPS data includes information regarding the driving environment, such as a type of environment (city, highway, rough terrain); and/or an imminent driving conditions (sharp corners, speed limit increases or decreases that require acceleration or de-acceleration). As another example, the vehicle's forward- and/or rear-facing radar can provide radar data to an ISS. The radar data includes information for detecting objects along a driving path, for example, to appear in an imminent driving environment. The vehicle's safety system provides vehicle safety data that includes information about the vehicle's airbags and seatbelts. The vehicle can provide environmental condition data such as current weather condition data, road condition data, and/or external light level data to the ISS. An ISS can also obtain these data from corresponding links provided by the vehicle.

E. Communication

1. Temperature and Physiological State

Temperature can affect an occupant's physiological state (e.g., alert, drowsy, asleep). Temperature gradients between a core skin temperature and a temperature of distal extremities (feet, hands) can facilitate transitions between physiological states. During the day, distal skin temperature is preferred to be approximately 2° C. cooler than proximal skin near the core. Cooling an occupant's feet and hands while warming the occupant's core will help increase alertness, whereas reversing this gradient (heating the feet and hands while cooling the core) will encourage relaxation. These gradients are achieved by temperature units in the ISS, as well as a connection with the zoned temperature control of the vehicle. According to temperature measurements and estimates such as an occupant's core skin temperature estimate, a temperature surrounding the ISS, an ambient temperature inside the vehicle, and/or a temperature of a vehicle zone (e.g., feet zone, hands zone, driver zone, or passenger zone) and desired temperatures corresponding to a desired physiological state, an ISS can adjust the temperature units in the ISS or of the vehicle.

2. Light Level Control and Physiological State

Blue-spectrum light interferes with the body's natural circadian rhythm; it aids to inhibit melatonin production and helps to maintains alertness. According to a current physiological state of an occupant and a desired physiological state, an ISS can adjust a light level of a dashboard of a vehicle. The ISS can regulate a spectrum and/or a brightness of the light emitted by the dashboard thereby to alert or awake a driver.

In alternate embodiments, aspects of the invention are implemented in computer hardware, firmware, software, and/or combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. A support system, comprising:
   an adjustable support device configured to support an occupant;
   one or more pressure sensors carried by the adjustable support device, the pressure sensors configured to measure pressure values on the adjustable support device;
   a processor carried by the adjustable support device; and
   memory storing instructions, the instructions, when executed by the processor, cause the processor to:
   receive the pressure values;
   input the pressure values into a machine learning model to determine a posture of the occupant, wherein determining the posture of the occupant comprises:
   determining a pressure distribution across the adjustable support device, extracting identifiable features in the pressure distribution, the identifiable features comprising pressure values of zones of the occupant,
   comparing the identifiable features to reference feature spaces constructed by analyzing pressure values collected for users in the users' past postures, and determining the posture of the occupant, the posture corresponding to at least a first state and a second state different from the first state; and
   cause an adjustment of the adjustable support device according to the posture of the occupant.

2. The support system of claim 1, wherein the pressure values correspond to surface pressure values.

3. The support system of claim 1, wherein the machine learning model is trained using one or more of the following: a history of the occupant's physiological states, a surrounding environment, or the occupant's preferences.

4. The support system of claim 1, wherein the instructions, when executed by the processor, cause the processor to determine a value of at least one of a heart rate, a breathing rate, or a body movement of the occupant.

5. The support system of claim 1, wherein the posture of the occupant is further determined by a machine vision process.

6. The support system of claim 5, wherein the machine vision process further comprises:
   extracting geometric features from the pressure values; and
   comparing the geometric features to reference posture images to select a predetermined posture position as the posture of the occupant, each reference posture image comprising geometric features for a corresponding predetermined posture position.

7. The support system of claim 1, wherein the support system is a seat configured to be installed in a vehicle.

8. The support system of claim 7, further comprising a plurality of sensors configured to generate sensor data including a driving environment.

9. The support system of claim 8, wherein the sensor data includes at least one of navigation data, radar data, vehicle safety data, weather data, road condition data, or external light level data from the vehicle, wherein the driving environment includes an external environment.

10. The support system of claim 1, wherein the adjustment of the adjustable support device comprises an adjustment of a shape of a seat surface of the adjustable support device to equalize pressure distribution on the seat surface.

11. The support system of claim 1, wherein the adjustment of the adjustable support device comprises an adjustment of a shape of a seat surface of the adjustable support device to conform to the posture of the occupant according to an occupant setting.

12. The support system of claim 1, wherein the adjustment of the adjustable support device comprises an adjustment of a first region and a second region of the adjustable support device separately for lumbar support and for cervical spine support.

13. A system comprising:
   an adjustable support device configured to support an occupant, the adjustable support device comprising pressure sensors carried by the adjustable support device, the pressure sensors configured to measure pressure values on the adjustable support device;
   a processor; and
   memory storing instructions, the instructions, when executed by the processor, cause the processor to:
   receive the pressure values;
   input the pressure values into a machine learning model to determine a posture of the occupant, wherein determining the posture of the occupant comprises:
   determining a pressure distribution across the adjustable support device,
   extracting identifiable features in the pressure distribution, the identifiable features comprising pressure values of zones of the occupant,
   comparing the identifiable features to reference feature spaces constructed by analyzing pressure values collected for users in the users' past postures, and
   determining the posture of the occupant, the posture corresponding to at least a first state and a second state different from the first state; and
   cause an adjustment of the adjustable support device according to the posture of the occupant.

14. The system of claim 13, further comprising a dashboard, wherein the instructions are further configured to cause the processor to adjust a light level of the dashboard according to a physiological state of the occupant.

15. The system of claim 14, wherein the physiological state is selected from a group comprising awake, drowsy, and asleep.

16. The system of claim 13, further comprising a steering wheel, wherein the adjustment of the adjustable support device comprises an adjustment of a distance of a seat surface of the adjustable support device to the steering wheel.

17. The system of claim 13, further comprising a temperature sensor, wherein the instructions, when executed by the processor, further cause the processor to adjust a temperature.

18. The system of claim 13, wherein the adjustment of the adjustable support device comprises an adjustment of a first region and a second region of the adjustable support device separately for lumbar support and for cervical spine support.

19. The system of claim 13, wherein the support system is a seat configured to be installed in a vehicle.

20. The system of claim 13, wherein the posture of the occupant is further determined by a machine vision process.

\* \* \* \* \*